US010085832B2

(12) United States Patent
Zaldivar

(10) Patent No.: US 10,085,832 B2
(45) Date of Patent: Oct. 2, 2018

(54) INTRAOCULAR LENS

(71) Applicant: SMARTECH I, LLC, Miami, FL (US)

(72) Inventor: Roger Zaldivar, Miami, FL (US)

(73) Assignee: Smartech I, LLC, Miami, FL (US)

( * ) Notice: Subject to any disclaimer, the term of this patent is extended or adjusted under 35 U.S.C. 154(b) by 0 days.

(21) Appl. No.: 14/874,770

(22) Filed: Oct. 5, 2015

(65) Prior Publication Data
US 2016/0095699 A1    Apr. 7, 2016

Related U.S. Application Data

(60) Provisional application No. 62/059,546, filed on Oct. 3, 2014.

(51) Int. Cl.
*A61F 2/16*  (2006.01)
(52) U.S. Cl.
CPC ............ *A61F 2/1601* (2015.04); *A61F 2/161* (2015.04); *A61F 2002/1689* (2013.01)
(58) Field of Classification Search
CPC .......................... A61F 2/1601; A61F 2/16015
See application file for complete search history.

(56) References Cited

U.S. PATENT DOCUMENTS

| 4,585,456 A | 4/1986 | Blackmore |
| 5,258,025 A | 11/1993 | Fedorov et al. |
| 5,480,428 A | 1/1996 | Fedorov et al. |
| 5,913,898 A | 7/1999 | Feingold |
| 6,106,553 A | 8/2000 | Feingold |
| 6,506,212 B2 | 1/2003 | Zhou et al. |
| 2007/0244560 A1* | 10/2007 | Ossipov ............... A61F 2/1601 623/6.14 |

OTHER PUBLICATIONS

Search Report for PCT/US2015/053948, filed Oct. 5, 2015, report dated Dec. 29, 2015, 2pp.
Written Opinion for PCT/US2015/053948, filed Oct. 5, 2015, opinion dated Dec. 29, 2015, 5pp.

* cited by examiner

*Primary Examiner* — Leslie Lopez
(74) *Attorney, Agent, or Firm* — Brinks Gilson & Lione

(57) ABSTRACT

An improved posterior chamber phakic intraocular lens (PCP-IOL) having a haptic with a collar, self-adjusting struts, and lens is disclosed. Haptic or lens of the PCP-IOL may include a protected orifice. A disclosed PCP-IOL may be configured to fit anatomy of varying sizes, and may be self-centering; additionally, a PCP-IOL as set forth herein may allow peripheral aqueous flow between anterior and posterior chambers of a patient's eye.

20 Claims, 8 Drawing Sheets

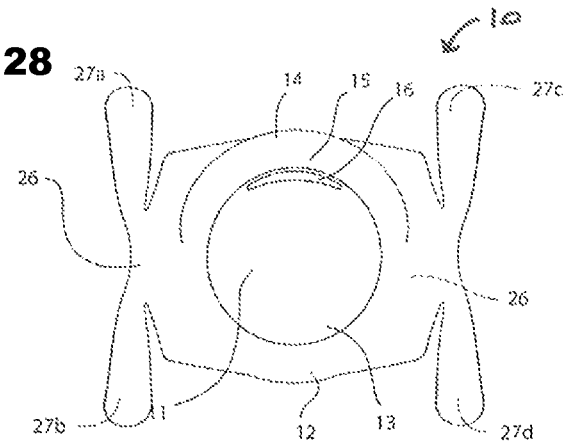
FIG. 28
FIG. 29
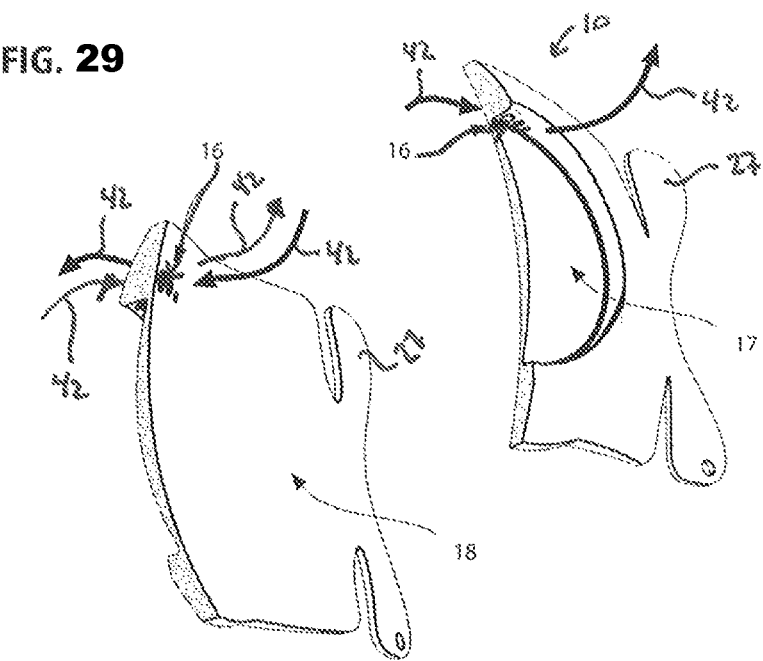
FIG. 30

INTRAOCULAR LENS

CROSS-REFERENCE TO RELATED APPLICATIONS

This application claims the benefit of U.S. provisional patent application Ser. No. 62/059,546, filed Oct. 3, 2014, the entire contents of which are herein incorporated by reference.

FIELD OF THE DISCLOSURE

Aspects of the present disclosure relate generally to intraocular lenses, and more particularly to a posterior chamber phakic intraocular lens (PCP-IOL) which is implanted in surgeries for correcting ametropia and presbyopia in human beings.

BACKGROUND

Traditionally, contact lenses were developed and marketed to be used on the external surface of the eye. Contact lenses were first manufactured using glass, although this was later substituted with biocompatible materials that minimize any reaction of the eye. Subsequently, the aphakic intraocular lens ("IOL") was invented to replace the natural lens due to eye problems such as cataracts. Further development led to the posterior chamber phakic intraocular lens ("PCP-IOL"), which was particularly useful in younger patients having a functional natural lens.

Even after decades of development, however, PCP-IOLs suffer from a number of persistent drawbacks and shortcomings. In some instances, those drawbacks lead to serious complications for patients.

One drawback relates to the sizing of a PCP-IOL for a patient's specific anatomy. The challenge in sizing PCP-IOLs is that the ciliary sulcus, where the PCP-IOL is to be positioned, is significantly different from person to person. In fact, the size of the ciliary sulcus typically ranges between 10.5 mm and 13 mm. If a physician implants an undersized PCP-IOL for the patient's anatomy (FIGS. 20-21), the PCP-IOL may inadvertently contact the surface of the natural lens, thus affecting the precision of the lens system and possibly causing cataract formation. In addition, in cases involving PCP-IOLs for correcting astigmatism, an undersized lens can result in loss of corrective power of the PCP-IOL.

On the other hand, if a physician implants an oversized PCP-IOL for the patient's anatomy (FIG. 22-23), the PCP-IOL may result in complications as severe as glaucoma by pupillary blockage. In some cases, an oversized PCP-IOL leads to other complications. For example, implanting an oversized PCP-IOL can lead to pressure decompensation between the anterior and posterior chambers of the eye due to the pupillary blockage of the aqueous humor by the anterior part of the PCP-IOL, on the trabeculum. To avoid such blockage, physicians often perform an iridectomy in connection with a PCP-IOL implantation. An iridectomy is a surgical puncture of the iris that establishes a passageway for the proper flow of aqueous between the anterior chamber and the posterior chamber. However, to resolve the blockage problem without creating other complications, the iridectomy requires a highly skilled and experienced physician. Iridectomies are often times painful, or at least appreciably uncomfortable, for the patient.

As an alternative to an iridectomy, certain PCP-IOLs have been created with a central hole in the lens that allows flow of aqueous between the anterior and posterior chambers, considerably improving the pressure compensation or equalization between the chambers. But such a hole in the lens seriously degrades lens quality because it causes light scattering and dazzling. This, in turn, results in positive and/or negative dysphotopsia.

Yet another drawback with certain prior art PCP-IOLs is that they have an anterior surface or other parts that rasp or restrict movement of the iris during dilation of the pupil, thus causing depigmentation.

BRIEF SUMMARY OF THE DISCLOSURE

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the embodiments disclosed herein; its sole purpose is to present some concepts of the disclosure in a simplified form as a prelude to the more detailed description that is presented later.

One or more of the preceding drawbacks of currently available PCP-IOLs are improved and an advance is made in the art by a novel PCP-IOL. According to one aspect of the disclosed embodiments, a PCP-IOL includes a haptic, adjustable struts, a collar, a lens, and a passageway that communicates between the front and back of the PCP-IOL.

In accordance with one embodiment, a PCP-IOL generally comprises: a smooth and continuous collar over a haptic, the collar having a steep inclination with smooth edges towards a lens zone. In use, the collar creates a "tent" or pocket between the posterior face of the iris and the anterior surface of the PCP-IOL, allowing for natural positioning. The presence of one or more peripheral orifices, slits, passageways, or holes that connect an anterior surface and a posterior surface of the PCP-IOL may facilitate the passage of the aqueous humor. The positioning of such an orifice may eliminate or reduce dysphotopsic effects as set forth below. In some embodiments, both the haptic and the lens zones form a substantially continuous surface, adjusting smoothly to the anterior surface of the crystalline lens.

As disclosed herein, a haptic region includes two zones: proximal wings and distal adjustable struts that are partially separated from the wings. The shape and flexibility of the adjustable struts may allow for compression radially towards the lens, enhancing adaptation of PCP-IOL 10 to the ciliary sulcus.

The following description and the appended drawings set forth certain illustrative aspects of the implementations presented in the disclosure. These aspects are indicative, however, of but a few of the various ways in which the principles of the disclosure may be employed, and the various embodiments are intended to include all such aspects and their equivalents. Other advantages and novel features will become apparent from the following description when considered in conjunction with the drawings.

BRIEF DESCRIPTION OF THE DRAWING FIGURES

FIG. 28 is a top view of a PCP-IOL in accordance with an embodiment having self-adjusting struts.

FIG. 29 is a cross-sectional perspective bottom view of a PCP-IOL having passages permitting aqueous flow between the anterior and posterior chambers of a patient's eye.

FIG. 30 is a cross-sectional perspective front view of a PCP-IOL having passages permitting aqueous flow between the anterior and posterior chambers of a patient's eye.

DETAILED DESCRIPTION

The following detailed description and the appended drawings describe and illustrate some implementations for the purpose of enabling one of ordinary skill in the relevant art to make and use these implementations. As such, the detailed description and drawings are purely illustrative in nature and are in no way intended to limit the scope of the disclosure in any manner. It should also be understood that the drawings are not necessarily to scale and in certain instances details, which are not necessary for an understanding of the disclosure, may have been omitted, such as details of fabrication and assembly.

Figure 1:
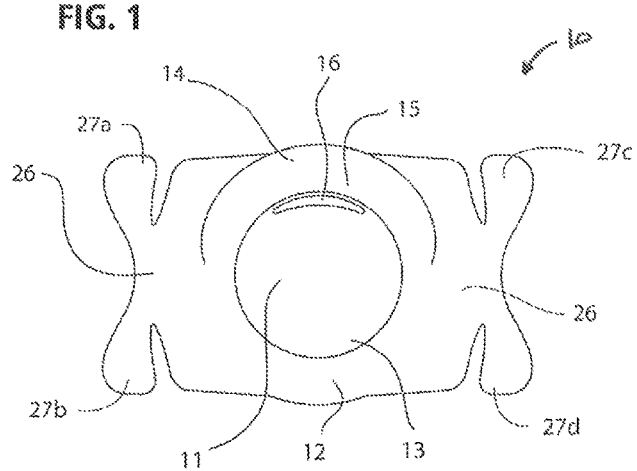
FIG. 1 is a front view showing a meniscus lens of a PCP-IOL in accordance with one embodiment.

In general, FIGS. 1-19 and 24-30 illustrate a posterior chamber phakic intraocular lens ("PCP-IOL") 10 that adapts to an eye's anatomy to facilitate correction and treatment of ametropia and presbyopia, for example, or to ameliorate or minimize the effects of other eye disorders or vision deficiencies. In some embodiments, PCP-IOL 10 has a haptic 12, a central lens 11 and an orifice 16 between an anterior surface and a posterior surface of PCP-IOL 10. As illustrated in FIG. 1, haptic 12 may comprise an elevated collar 14, wings 26, radially-elastic, adaptable struts 27a-d, and a central lens 11. A peripheral orifice 16 (defining an opening or passage between an anterior surface and a posterior surface of PCP-IOL 10) may be positioned proximate collar 14 and may be generally operative to allow aqueous flow either through lens 11 (e.g., FIGS. 1, 4, and 15) or collar 14 itself (e.g., FIGS. 5, 6, 24, 27, 29). Lens 11 may be secured to the structure of haptic 12 in any of various ways generally known in the art; in that regard, the term "secured" in this context is intended to refer to any suitable technology or method operative to secure, fixedly attach, integrate, or otherwise to fuse or join lens 11 with haptic 12 consistent with their interoperability as are known in the art or developed in accordance with known principles.

Figure 7:
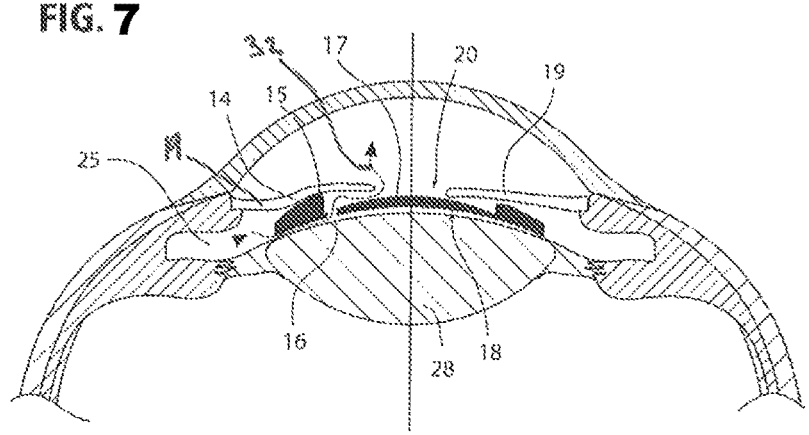
FIG. 7 is a side view cut of an eye with a PCP-IOL having a passage of the aqueous humor from the posterior chamber to the anterior chamber, and the "tent" produced by the iris and the PCP-IOLs ridged.

Referring to FIG. 7, orifice 16 may permit aqueous flow (depicted by arrows 32) between the anterior and posterior chambers of the eye, while collar 14 protects the opening of orifice 16 by deflecting iris 19 away from orifice 16. This deflection may serve to prevent iris 19 from occluding, obstructing, sealing or otherwise adhering to orifice 16 in a way that dangerously limits aqueous flow between the anterior and posterior chambers when the pupil is constricted. Struts 27 facilitate sizing of PCP-IOL 10 to the size of a patient's ciliary sulcus. Struts 27 may also function dynamically to position PCP-IOL 10, and in particular, to center lens 11, relative to a patient's natural lens.

FIG. 1 illustrates one embodiment of haptic 12, which forms a platform for PCP-IOL 10. Haptic 12 is formed from any suitable flexible, biocompatible material (which has appropriate or desired optical qualities or lensing characteristics) that will be known to those of skill in the pertinent art. The surface of haptic 12 (and in particular, the surface of collar 14 that is in contact with iris 19) is preferably substantially smooth and curvilinear in order to preserve the pigmentation by avoiding a rough rubbing of iris 19 by haptic 12, in general, and collar 14, in particular. The shape and flexibility of PCP-IOL 10 allows it to be folded and unfolded by a physician to permit implantation in an eye.

Figure 24:
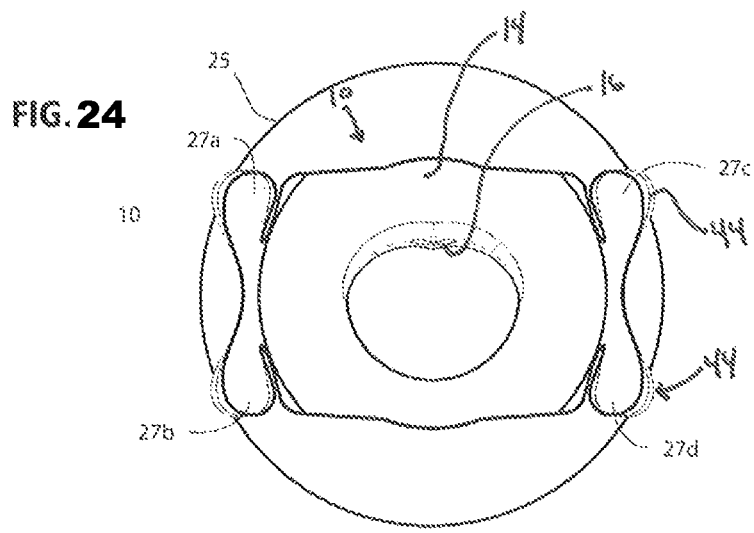
FIG. 24 illustrates a top view of a PCP-IOL in accordance with an embodiment relative to a patient's ciliary sulcus.
Figure 25:
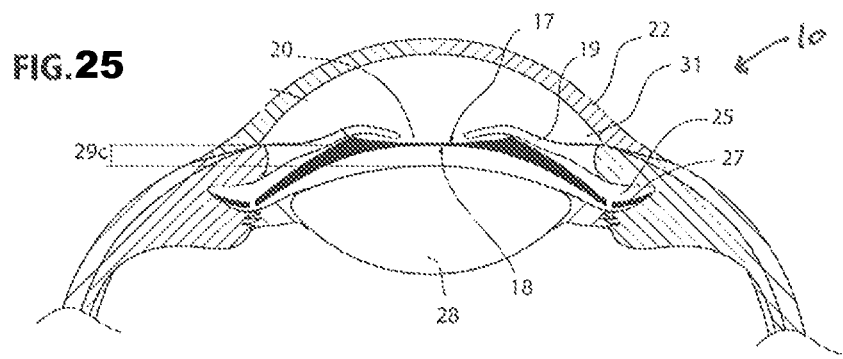
FIG. 25 illustrates a cross-sectional lateral view of a PCP-IOL in accordance with an embodiment relative to a patient's eye.
Figure 26:
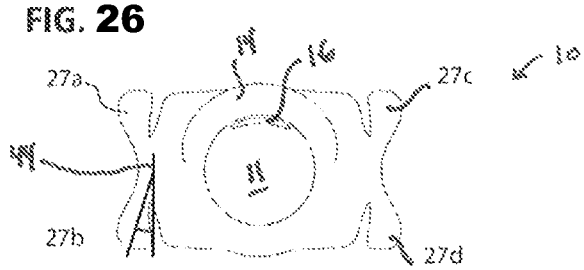
FIG. 26 is a top view of a PCP-IOL in accordance with an embodiment having self-adjusting struts.
Figure 27:
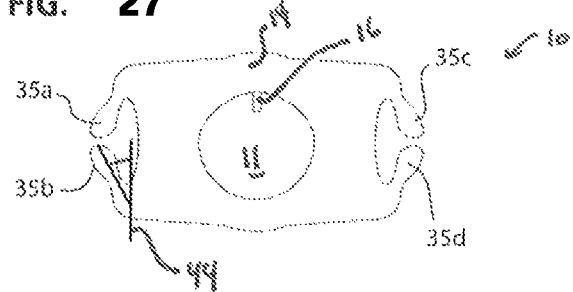
FIG. 27 is a top view of a PCP-IOL in accordance with an embodiment having self-adjusting struts.

Haptic 12 includes lateral wings 26 and elastic struts 27a-d spaced apart from wings 26. Struts 27a-d of haptic 12 may be provided in different sizes, some being relatively shorter (FIG. 26) or relatively longer (FIG. 28) than others. Additionally or alternatively, struts 27a-d may be diverging (FIG. 26) or converging (FIG. 27). The radial elasticity of struts 27a-d permits flexing of the struts 27a-d in a way that reduces the exterior size of PCP-IOL 10, as shown in FIGS. 24 and 25. As shown in FIGS. 26-27, the radial elasticity of struts 27a-d results in a range of motion (represented by the angle indicated at reference numeral 44). Struts 27a-d therefore provide significant tolerance or adaptability in use. In some embodiments, struts 27a-d allow adjustment between about 5 microns and about 3000 microns. Such tolerance facilitates achieving a preferred 0.3 mm-0.8 mm space or gap (known as "vaulting") between lens 11 and an eye's natural lens even when there are differences between the predicted and actual size of the ciliary sulcus 25. Struts 27a-d also act to center and position lens 11 relative to the natural lens. Struts 27 can be provided at an angle between 0 degrees and 90 degrees relative to haptic 12. It is noted that the particular size, shape, orientation, and range of motion 44 of struts 27a-d may vary in accordance with eye anatomy, material selection, governmental or health code regulations, or a combination of these and other factors. The present disclosure is not intended to be limited by any particular configuration of struts 27a-d.

Figure 3:
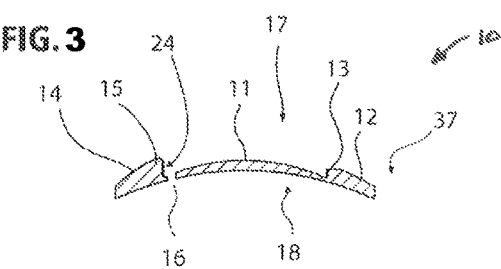
FIG. 3 is a top view cut of the PCP-IOL of FIG. 1.
Figure 4:
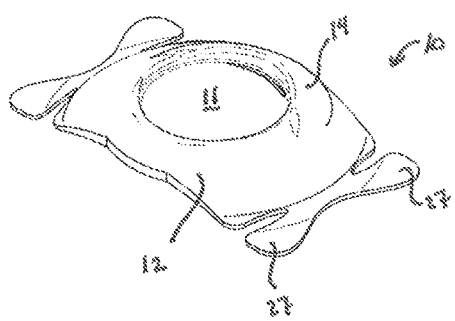
FIG. 4 is a perspective view of the PCP-IOL of FIG. 1.
Figure 8:
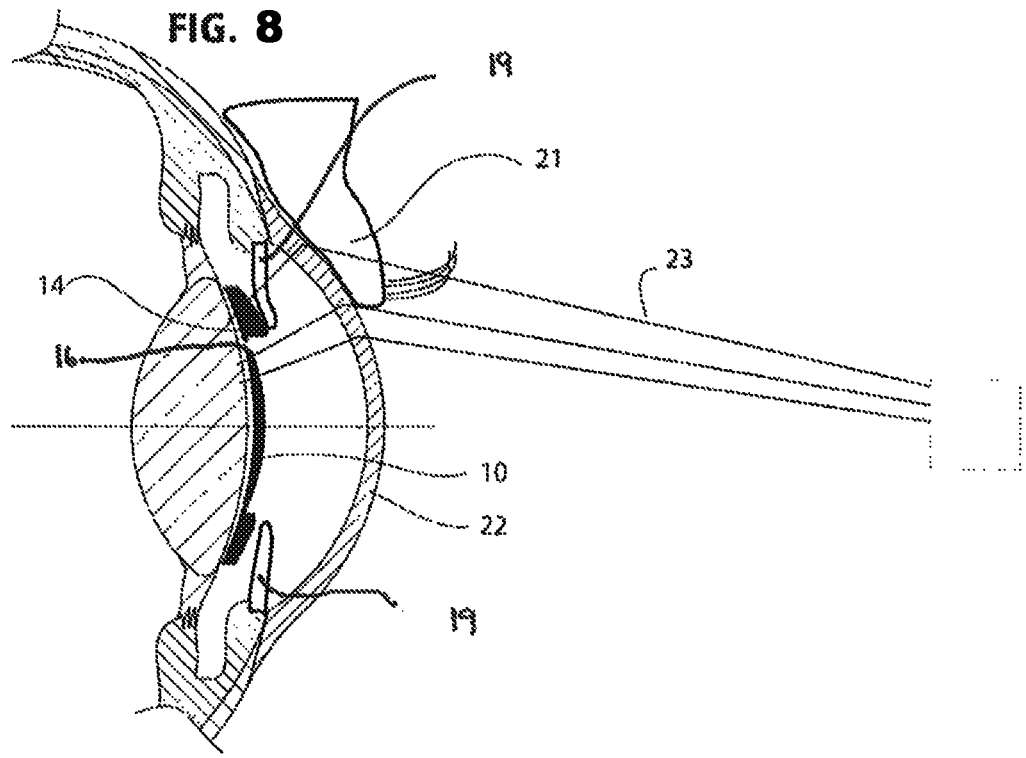
FIG. 8 is a side view cut of an eye with an eyelid, demonstrating the light's projection through the lensal system of one embodiment.
Figure 9:
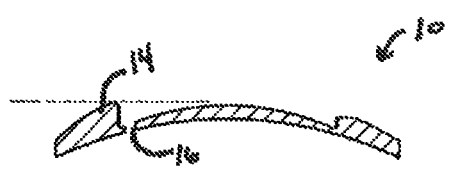
FIGS. 9-11 illustrate cross-sectional side views of several PCP-IOLs in accordance with disclosed embodiments.
Figure 10:
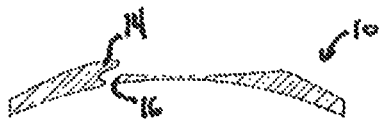
Figure 11:
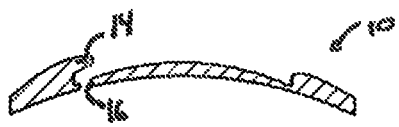
Figure 12:
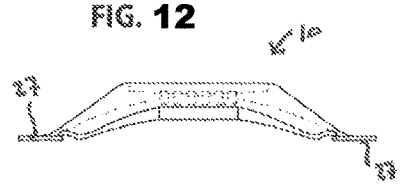
FIG. 12 is a side view of a PCP-IOL in accordance with an embodiment.
Figure 13:
FIG. 13 is a cross-sectional side view of a PCP-IOL in accordance with an embodiment.
Figure 14:
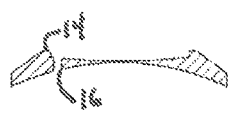
FIG. 14 is a cross-sectional side view of a PCP-IOL in accordance with an embodiment.

As best illustrated in FIGS. 1 and 3, haptic 12 may further include an elevated collar 14 forming a curved wall. The ends and surface of collar 14 may be smoothly sloped, curved, or graded into the structure of haptic 12, as illustrated in the embodiments of FIGS. 1, 5, and 9-11. Such sloping allows collar 14 gently to bias or direct iris 19 away from orifice 16 without causing depigmentation. For example, as illustrated in FIG. 7, when the pupil is constricted, collar 14 protects orifice 16 from penetration by iris 19. That is, as the posterior surface of iris 19 slides over collar 14, the elevation of collar 14 (as compared to other portions of haptic 12) creates a natural chamber or tented region, allowing iris 19 to extend past orifice 16 without clogging, obstructing, occluding, or otherwise interfering with same. Because iris 19 passes over, but does not penetrate or directly obstruct orifice 16, it does not create a seal over orifice 16 or adhere to it. In some implementations, collar 14 also protects orifice 16 from obstruction when the pupil is dilated as shown in FIG. 8. This allows flow of aqueous at all times.

Figure 15:
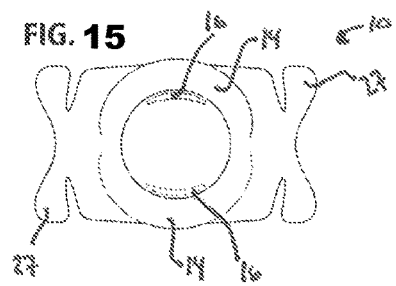
FIG. 15 is a top view of a PCP-IOL in accordance with an embodiment.
Figure 16:
FIG. 16 is a side view of a PCP-IOL for use in correcting myopic conditions.
Figure 17:
FIG. 17 is a side view of a PCP-IOL in accordance with an embodiment.
Figure 18:
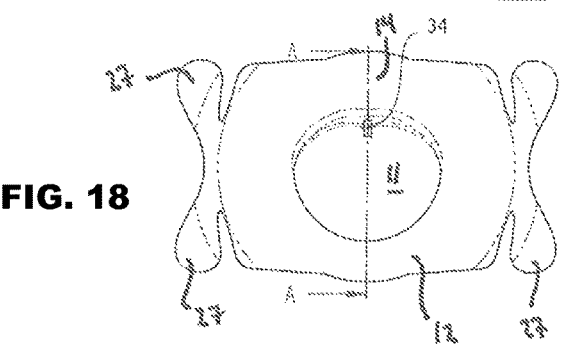
FIG. 18 is a perspective top view of a PCP-IOL in accordance with an embodiment.
Figure 19:
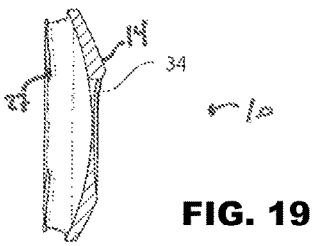
FIG. 19 is a cross-sectional side view of the PCP-IOL of FIG. 18 taken along an axis A-A.
Figure 20:
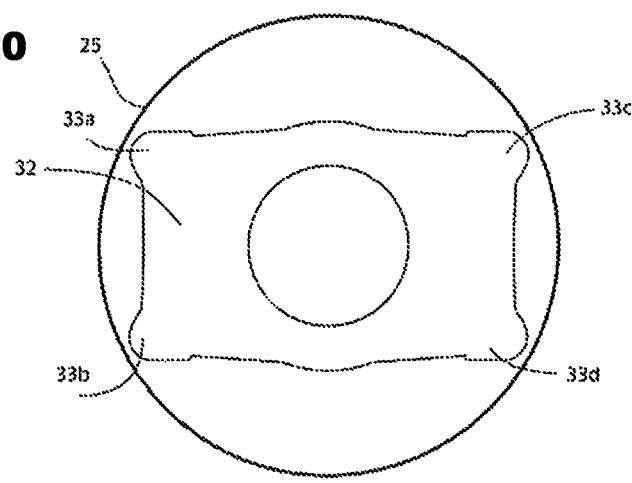
FIG. 20 is a top view of a prior art PCP-IOL that is undersized relative to a patient's ciliary sulcus.
Figure 21:
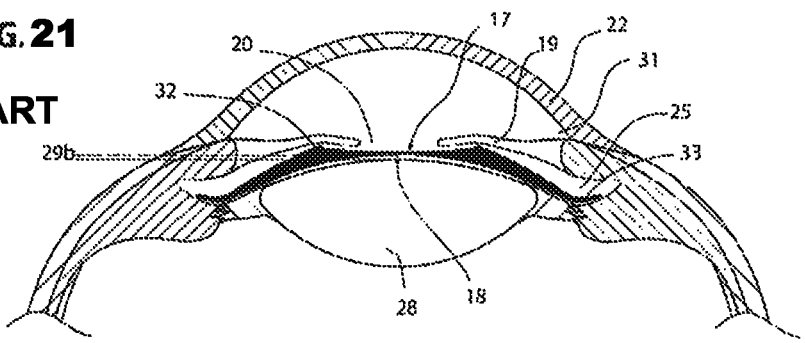
FIG. 21 illustrates a cross-sectional lateral view of a prior art PCP-IOL that is undersized relative to a patient's eye, and in near or actual contact with the patient's natural lens.
Figure 22:
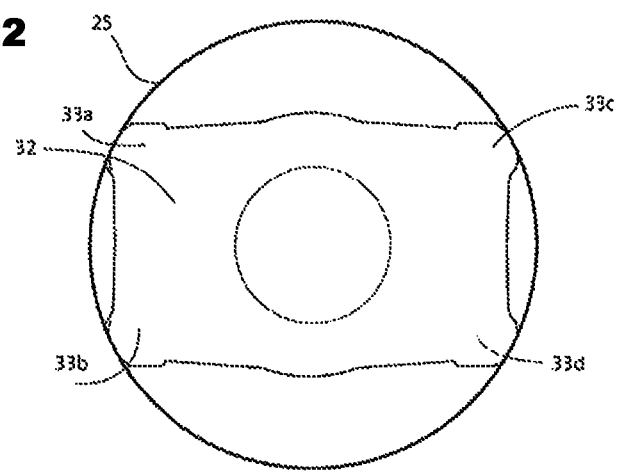
FIG. 22 is a top view of a prior art PCP-IOL that is oversized relative to a patient's ciliary sulcus.
Figure 23:
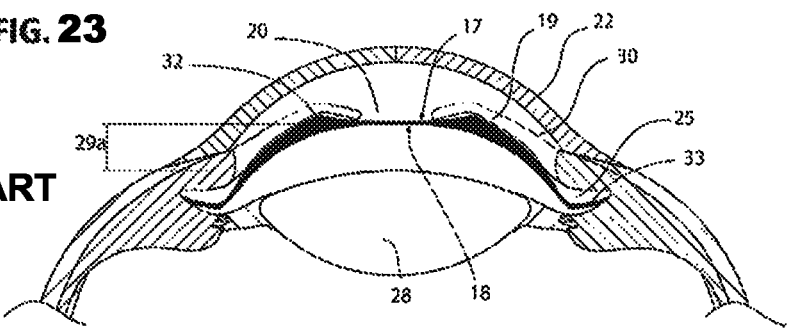
FIG. 23 illustrates a cross-sectional lateral view of a hyper-vaulting prior art PCP-IOL that is oversized relative to a patient's eye.

Collar 14 may be a circumferential collar, or ring, that extends around all or substantially all of the circumference of lens 11 as shown in FIG. 15, for example. In alternative embodiments, collar 14 may be implemented as a partial collar that extends around some portion of lens 11. FIG. 1, for example, illustrates an embodiment having an asymmetrical partial collar 14 in a superior portion of PCP-IOL 10. As yet another alternative, collar 14 may be formed as an elevation or bulge, as shown in FIG. 18. In still other embodiments, collar 14 may be positioned laterally beside lens 11.

Figure 5:
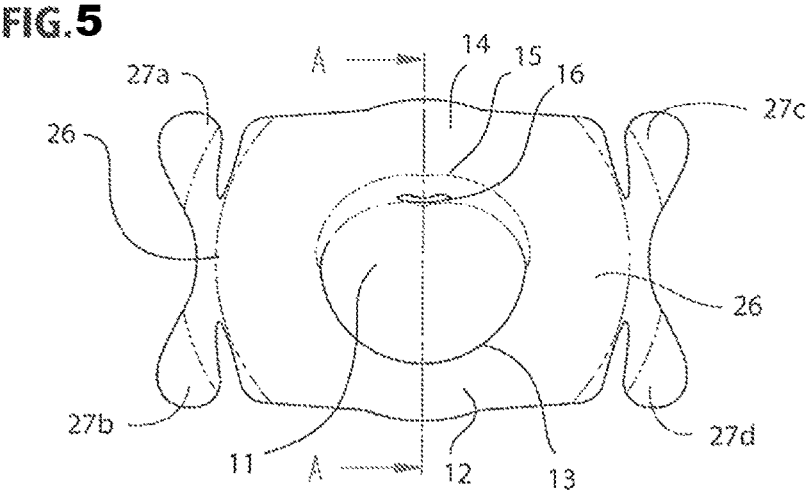
FIG. 5 is a front view of a PCP-IOL with a biconcave lens in accordance with one embodiment.

Orifice 16 may be provided through lens 11 as a slit, hole, or other suitable passageway; it is noted that it may be desirable in some embodiments to implement orifice 16 as a series or plurality of holes, slits, passageways, or perforations. By way of example, FIGS. 1, 4, 15, and 27 illustrate orifice 16 as a slit or crescent or U-shaped opening through lens 11. Alternatively, orifice 16 may be provided through haptic 12, and more specifically, through a wall at the intersection of haptic 12 and lens 11 (see FIG. 3). For example, FIGS. 5, 18, and 24 show orifice 16 as a passageway through haptic 12. As noted above, multiple orifices may be provided in lens 11; alternatively, an orifice 16 (or more than one) may be provided in both lens 11 and haptic 12. Various configurations are contemplated, and the present disclosure is not intended to be limited to any particular location or configuration of a single instance or multiple instances of orifice 16.

Referring to FIG. 8, a superior location of orifice 16 may limit usual dysphotopsic effects because orifice 16 is concealed under the eyelid's shadow cone. That is, certain strategic positioning of orifice 16 may limit unwanted light scattering or dazzling effects in some instances because light rays 23 entering the eye are substantially or entirely blocked by the natural position of the open eyelid 21. Further, when the pupil is constricted, iris 19 may fully block light from entering orifice 16.

FIG. 3 shows that the elevation (or "height") 15 of a ridge associated with collar 14, in order to create a tent above an anterior surface 17 of lens 11 proximal to orifice 16, is such that it can create a greater unevenness 24 between a transition zone 13 and lens 11, depending on the dioptric power and shape of the lens 11. The unevenness 24 may be provided with smooth or rounded sides in order to achieve a soft rubbing with low friction against iris 19. In the foregoing manner, it is possible to enable aqueous humor to flow through orifice 16 in the tented region.

Figure 2:
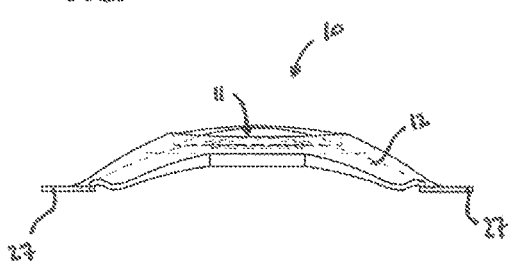
FIG. 2 is a top view of the PCP-IOL of FIG. 1.

Some embodiments may be adapted for use with a lens having a positive (+) meniscus. As shown in FIGS. 2 and 3, for a convex lens 11, a periphery of lens 11 can be positioned in a posterior plane 37. That is, lens 11 is "sunken" or recessed in haptic 12. This is because the pupil contracts and iris 19 gets closer to the highest elevation area of lens 11. This elevation area is preferably at the same or at a lower level of collar 14 to produce the tenting effect discussed above. As noted above, PCP-IOL 10 is generally manufactured of biocompatible materials and comprises a lens component (lens 11), a two-zone haptic component (comprising haptic 12 and collar 14), and a transitional area between these two parts (such as represented by reference numerals 24 and 13 in FIG. 3).

Figure 6:
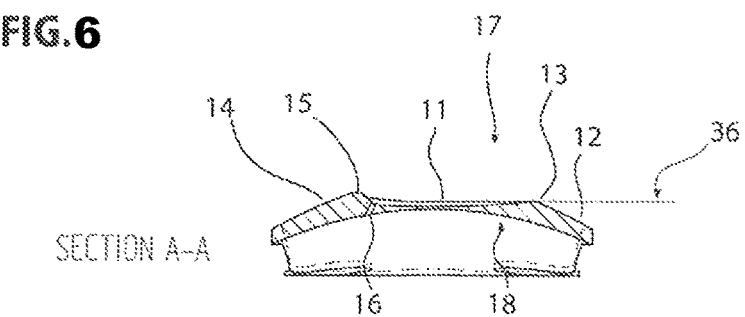
FIG. 6 is a side view cut of the PCP-IOL of FIG. 2.

Alternative embodiments may be adapted for use in connection with lenses having a negative (−) biconcave surface. As shown in FIG. 6, where there is a thinning in the central area of lens 11 (i.e., the lens is positioned lower with respect to its boundary) the periphery of lens 11 may be located in a continuous mode regarding the anterior part of haptic 12.

The descriptions set forth above are meant to be illustrative and not limiting. Various modifications, in addition to those described herein, will be apparent to those skilled in the art from the foregoing description. Such modifications are also intended to fall within the scope of the concepts described herein. Each patent, patent application and publication cited or described in this document are hereby incorporated herein by reference, in their entireties.

The foregoing description of possible implementations consistent with the present disclosure does not represent a comprehensive list of all such implementations or all variations of the implementations described. The description of one implementation should not be construed as an intent to exclude other implementations. For example, artisans will understand how to implement the illustrative examples in many other ways, using equivalents and alternatives that do not depart from the scope of the disclosure. Moreover, unless indicated to the contrary in the preceding description, none of the components described in the implementations are essential to the arrangements disclosed. It is thus intended that the disclosed embodiments be considered as illustrative, with a true scope and spirit of the disclosure being indicated by the following claims.

What is claimed is:

1. An intraocular medical device having an anterior surface and a posterior surface, the intraocular medical device comprising:
   a haptic body having a strut and an anteriorly elevated collar;
   a lens secured to the haptic body; and
   the collar extends anteriorly beyond the lens; and
   a passageway extending between the anterior surface and the posterior surface;
   wherein the elevated collar is capable of creating a tented region over the passageway when an eye's iris passes over said collar, allowing the iris to extend over the passageway without clogging, obstructing, occluding or interfering with the passageway;

wherein:
the lens is surrounded by the haptic body and its collar;
the tented region has a thickness along an optical axis that is greater than a length of the passageway between the anterior and posterior surfaces; and
aqueous flow is permitted through the passageway.

2. The intraocular medical device of claim 1, wherein the passageway extends through the collar or through the lens.

3. The intraocular medical device of claim 2, wherein the passageway extends through the collar.

4. The intraocular medical device of claim 3, wherein the collar forms a crescent having tapered ends.

5. The intraocular medical device of claim 4, wherein the passageway has an elongate cross section.

6. The intraocular medical device of claim 5, wherein the lens is a positive meniscus or a negative meniscus.

7. The intraocular medical device of claim 6, wherein the lens is the positive meniscus.

8. The intraocular medical device of claim 6, wherein the lens is the negative meniscus.

9. The intraocular medical device of claim 1, wherein the passageway extends through the lens.

10. The intraocular medical device of claim 9, wherein the passageway is positioned beside the collar.

11. The intraocular medical device of claim 10, wherein the collar forms a crescent having tapered ends.

12. The intraocular medical device of claim 11, wherein the passageway is crescent shaped and is positioned beside the collar.

13. The intraocular medical device of claim 12, wherein the lens is a positive meniscus or a negative meniscus.

14. The intraocular medical device of claim 13, wherein the lens is the positive meniscus.

15. The intraocular medical device of claim 13, wherein the lens is the negative meniscus.

16. The intraocular medical device of claim 9, wherein the strut is adjustable through a distance between about 5 microns and about 3000 microns relative to the haptic body.

17. The intraocular medical device of claim 1, wherein the collar further protects the passageway from obstruction when an eye pupil is dilated.

18. An intraocular medical device having an anterior surface and a posterior surface, the intraocular medical device comprising:
a haptic body having a strut and an elevated collar;
a lens secured to the haptic body; and
a passageway extending between the anterior surface and the posterior surface;

wherein:
the elevated collar is capable of creating a tented region over the passageway when an eye's iris passes over said collar, allowing the iris to extend over the passageway without clogging, obstructing, occluding or interfering with the passageway;
the collar has a portion extending over the passageway radially inward toward the center of the lens;
the tented region has a thickness along an optical axis that is greater than a length of the passageway between the anterior and posterior surfaces; and
aqueous flow is permitted through the passageway.

19. The intraocular medical device according to claim 18, wherein the passageway extends through the lens.

20. The intraocular medical device according to claim 18, wherein the collar further protects the passageway from obstruction when an eye pupil is dilated.

* * * * *